(12) United States Patent
Goldsbrough

(10) Patent No.: US 6,878,818 B1
(45) Date of Patent: Apr. 12, 2005

(54) MODIFIED UBIQUITIN REGULATORY SYSTEM

(75) Inventor: Andrew Goldsbrough, Histon (GB)

(73) Assignee: Monsanto UK Ltd. (GB)

(*) Notice: Subject to any disclaimer, the term of this patent is extended or adjusted under 35 U.S.C. 154(b) by 414 days.

(21) Appl. No.: 10/069,909

(22) PCT Filed: Sep. 7, 2000

(86) PCT No.: PCT/EP00/08690

§ 371 (c)(1),
(2), (4) Date: Jun. 12, 2002

(87) PCT Pub. No.: WO01/18220

PCT Pub. Date: Mar. 15, 2001

(30) Foreign Application Priority Data

Sep. 9, 1999 (EP) ............................................. 99307158

(51) Int. Cl.⁷ ......................... C12N 15/82; A01H 5/00; A01H 5/10
(52) U.S. Cl. ................. 536/24.1; 536/23.1; 435/320.1; 435/419; 435/468; 800/278; 800/285; 800/298; 800/320; 800/320.1; 800/320.3
(58) Field of Search ............................ 536/2.31, 24.1; 435/320.1, 419, 468; 800/278, 285, 298, 320, 320.1, 320.3

(56) References Cited

FOREIGN PATENT DOCUMENTS

| EP | 0342926 | 11/1989 |
|----|---------|---------|
| WO | WO 00/15810 | 3/2000 |

OTHER PUBLICATIONS

Liu L. et al., "Characterization, Chromosomal Mapping, and Expression of Different Poly–Ubiquitin Genes in Tissues from Control and Heat–Shocked Maize Seedlings", *Biochemistry and Cell Biology*, 73(1&2):19–20 (1995).

Genschik P. et al., "Structure and Promoter Activity of a Stress and Developmentally Regulated Polyubiquitin–Encoding Gene of Nicotiana Tabacum", *Gene*, 148(2):195–202 (1994).

Kawallek P. et al., "Polyubiquitin Gene Expression and Structural Properties of the Ubi4–2 Gene in Petroselinum Crispum", *Plant Molecular Biology*, 21(4):673–684 (1993).

*Primary Examiner*—Amy J. Nelson
*Assistant Examiner*—Russell Kallis
(74) *Attorney, Agent, or Firm*—Howrey Simon Arnold & White, LLP

(57) ABSTRACT

A modified ubiquitin regulatory system which lacks heat-shock elements and so is not heat inducible can be used to regulate expression of a structural gene under the control thereof, e.g. by introducing an appropriate DNA construct into plant tissue.

10 Claims, 7 Drawing Sheets

```
agctgaatcc ggcggcatgg caaggtagac tgcagtgcag cgtgacccgg tcgtgcccct
ctctagagat aatgagcatt gcatgtctaa gttataaaaa attaccacat atttttttg
tcacacttgt ttgaagtgca gtttatctat ctttatacat atatttaaac tttactctac
gaataatata atctatagta ctacaataat atcagtgttt tagagaatca tataaatgaa
cagttagaca tggtctaaag gacaattggt attttgacaa caggactcta cagttttatc
tttttagtgt gcatgtgttc tcctttttt ttttgcaaat agcttcacct atataatact
tcatccattt tattagtaca tccatttagg gtttagggtt aatggttttt atagactaat
ttttttagta catctatttt attctatttt agcctctaaa ttaagaaaac taaaactcta
ttttagtttt tttatttaat aatttagata taaaatagaa taaaataaag tgactaaaaa
ttaaacaaat acccttaag aaattaaaaa aactaaggaa acatttttct tgtttcgagt
agataatgcc agcctgttaa acgccgtcga cgcagtctaa cggacaccaa ccagcgaacc
agcagcgtcg cgtcgggcca agcgaagcag acggcacggc atctctgtcg ctgcctggt
acdggacttc gtccgctgtc ggcatccaga aattgcgtgg cggagcggca gacgtgagcc
ggcacggcag gcggcctcct cctcctctca cggcaccggc agctacgggg gattcctttc
ccaccgctcc ttcgctttcc cttcctcgcc cgccgtaata aatagacacc ccctccacac
cctctttccc caacctcgtg ttgttcggag cgcacacaca cacaaccaga tctccccaa
atccacccgt cggcacctcc gcttcaaggt acgccgctcg tcctcccccc ccctctctac
cttctctaga tcggcgttcc ggtccatggt tagggcccgg tagttctact tctgttcatg
tttgtgttag atccgtgttt gtgttagatc cgtgctgcta gcgttcgtac acggatgcga
cctgtacgtc agacacgttc tgattgctaa cttgccagtg tttctctttg gggaatcctg
ggatggctct agccgttccg cagacgggat cgatttcatg attttttttg tttcgttgca
tagggtttgg tttgcccttt tcctttattt caatatatgc cgtgcacttg tttgtcgggt
catcttttca tgctttttt tgtcttggtt gtgatgatgt ggtctggttg ggcggtcgtt
ctagatcgga gtagaattct gtttcaaact acctggtgga tttattaatt ttggatctgt
atgtgtgtgc catacatatt catagttacg aattgaagat gatggatgga aatatcgatc
taggataggt atacatgttg atgcgggttt tactgatgca tatacagaga tgcttttgtt
cgcttggttg tgatgatgtg gtgtggttgg gcggtcgttc attcgttcta gatcggagta
gaatactgtt tcaaactacc tggtgtattt attaattttg gaactgtatg tgtgtgtcat
acatcttcat agttacgagt ttaagatgga tggaaatatc gatctaggat aggtatacat
gttgatgtgg gttttactga tgcatataca tgatggcata tgcagcatct attcatatgc
tctaaccttg agtacctatc tattataata aacaagtatg ttttataatt attttgatct
tgatatactt ggatgatggc atatgcagca gctatatgtg gattttttta gccctgcctt
catacgctat ttatttgctt ggtactgttt cttttgtcga tgctcaccct gttgtttggt
gttacttctg cagatgcaga tctttgtgaa aaccctgact ggcaagacta tca
```

FIG. 3

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
```
tcgcgatcca gactgaatgc c                                      21

<210> SEQ ID NO 2
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 2
attaggtacc ggacttgctc cgctgtcggc                             30

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
tataggtacc gaggcagcga cagagatgcc                             30

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 4
atatgctgca gtgccagcgt gacccgg                                27

<210> SEQ ID NO 5
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 5
tggacccctc tcgagagttc cgctccaccg tt                          32

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
agctgaatcc ggcggcatgg c                                      21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
tgatagtctt gccagtcagg g                                      21

<210> SEQ ID NO 8
<211> LENGTH: 2033
<212> TYPE: DNA

-continued

```
<213> ORGANISM: Zea Mays

<400> SEQUENCE: 8
agctgaatcc ggcggcatgg caaggtagac tgcagtgcag cgtgacccgg tcgtgcccct      60
ctctagagat aatgagcatt gcatgtctaa gttataaaaa attaccacat atttttttg     120
tcacacttgt ttgaagtgca gtttatctat ctttatacat atatttaaac tttactctac    180
gaataatata atctatagta ctacaataat atcagtgttt tagagaatca tataaatgaa    240
cagttagaca tggtctaaag gacaattggt attttgacaa caggactcta cagttttatc    300
ttttagtgt gcatgtgttc tcctttttt ttttgcaaat agcttcacct atataatact      360
tcatccattt tattagtaca tccatttagg gtttagggtt aatggttttt atagactaat    420
tttttagta catctatttt attctatttt agcctctaaa ttaagaaaac taaaactcta     480
ttttagtttt tttatttaat aatttagata taaaatagaa taaaataaag tgactaaaaa    540
ttaaacaaat acccttaag aaattaaaaa aactaaggaa acatttttct tgtttcgagt     600
agataatgcc agcctgttaa acgccgtcga cgcagtctaa cggacaccaa ccagcgaacc    660
agcagcgtcg cgtcgggcca agcgaagcag acggcacggc atctctgtcg ctgcctcggt    720
accggacttc gtccgctgtc ggcatccaga aattgcgtgg cggagcggca gacgtgagcc    780
ggcacggcag gcggcctcct cctcctctca cggcaccggc agctacgggg gattccttc     840
ccaccgctcc ttcgctttcc cttcctcgcc cgccgtaata aatagacacc ccctccacac    900
cctctttccc caacctcgtg ttgttcggag cgcacacaca cacaaccaga tctcccccaa    960
atccacccgt cggcacctcc gcttcaaggt acgccgctcg tcctccccc cctctctac    1020
cttctctaga tcggcgttcc ggtccatggt tagggcccgg tagttctact tctgttcatg   1080
tttgtgttag atccgtgttt gtgttagatc cgtgctgcta gcgttcgtac acggatgcga   1140
cctgtacgtc agacacgttc tgattgctaa cttgccagtg tttctctttg gggaatcctg   1200
ggatggctct agccgttccg cagacgggat cgatttcatg attttttttg tttcgttgca   1260
tagggtttgg tttgcccttt tcctttattt caatatatgc cgtgcacttg tttgtcgggt   1320
catcttttca tgctttttt tgtcttggtt gtgatgatgt ggtctggttg ggcggtcgtt   1380
ctagatcgga gtagaattct gtttcaaact acctggtgga tttattaatt ttggatctgt   1440
atgtgtgtgc catacatatt catagttacg aattgaagat gatggatgga aatatcgatc   1500
taggataggt atacatgttg atgcgggttt tactgatgca tatacagaga tgcttttgtt   1560
cgcttggttg tgatgatgtg gtgtggttgg gcggtcgttc attcgttcta gatcggagta   1620
gaatactgtt tcaaactacc tggtgtattt attaattttg gaactgtatg tgtgtgtcat   1680
acatcttcat agttacgagt ttaagatgga tggaaatatc gatctaggat aggtatacat   1740
gttgatgtgg gttttactga tgcatataca tgatggcata tgcagcatct attcatatgc   1800
tctaaccttg agtacctatc tattataata aacaagtatg ttttataatt attttgatct   1860
tgatatactt ggatgatggc atatgcagca gctatatgtg gattttttta gccctgcctt   1920
catacgctat ttatttgctt ggtactgttt cttttgtcga tgctcaccct gttgtttggt   1980
gttacttctg cagatgcaga tctttgtgaa aaccctgact ggcaagacta tca          2033
```

MODIFIED UBIQUITIN REGULATORY SYSTEM

This application is a §371 national stage filing of PCT/EP00/08690, filed 7 Sep. 2000 (published in English on 15 Mar. 2001 as WO 01/18220) and claiming priority to EP 99307158.8 filed 9, September 1999.

FIELD OF THE INVENTION

This present invention relates in general to gene expression and is in particular concerned with regulatory systems for regulating gene expression based on the ubiquitin regulatory system (URS) and the use of these regulatory systems in combination with an expressible structural gene, preferably a plant expressible structural gene, for the regulated expression of said structural gene and for a regulated expression control when stressed for instance with elevated temperature.

BACKGROUND OF THE INVENTION

Genetic Engineering of Plants

The hurdle of creating successful genetically engineered plants in major crop varieties is now being overcome sequentially on a plant-by-plant basis. The term "genetic engineering" is meant to describe the manipulation of the genome of a plant, typically by the introduction of a foreign gene into a plant, or the modification of the genes of the plant, to increase or decrease the synthesis of gene products in the plant. Typically, genes are introduced into one or more plant cells which can be cultured into whole, sexually competent, viable plants which may be totally transformed or which may be chimeric, having some tissues transformed and some not. These plants can be self-pollinated or cross-pollinated with other plants of the same or compatible species so that the foreign gene or genes carried in the germ line can be bred into agriculturally useful plant varieties.

Current strategies directed toward the genetic engineering of plant lines typically involve two complementary processes. The first process involves the genetic transformation of one or more plant cells of a specifically characterized type. The term "transformation" as used herein means that a foreign gene, typically in the form of a genetic construction, is introduced into the genome of the individual plant cells.

This introduction is accomplished through the aid of a vector, which is integrated into the genome of the plant. The second process then involves the regeneration of the transformed plant cells into whole sexually competent plants. Neither the transformation nor regeneration process need to be 100% successful, but must have a reasonable degree of reliability and reproducibility so that a reasonable percentage of the cells can be transformed and regenerated into whole plants.

EP-A0342926 (the content of which is incorporated herein by reference) discloses a plant (maize) ubiquitin regulatory system comprising a heatshock element (comprising two overlapping consensus heatshock elements), a promoter, a transcription start site, an intron and a translation start site. The heatshock element component of this regulatory system is believed to confer heat inducibility of expression of associated DNA sequences in dicot or monocot cells following permissive levels of heatshock.

Plant ubiquitin regulatory system refers to the approximately 2 kb nucleotide sequence 5' to the translation start site of the ubiquitin gene and comprises sequences that direct initiation of transcription, control of expression level, induction of stress genes and enhancement of expression in response to stress. The regulatory system, comprising both promoter (of about 1 kb nucleotide sequence) and regulatory functions, is the DNA sequence providing regulatory control or modulation of gene expression. A structural gene placed under the regulatory control of the plant ubiquitin regulatory system means that a structural gene is positioned such that the regulated expression of the gene is controlled by the sequences comprising the ubiquitin regulatory system.

Promoters are DNA elements that direct the transcription of RNA in cells. Together with other regulatory elements that specify tissue and temporal specificity of gene expression, promoters control the development of organisms.

There has been a concerted effort in identifying and isolating promoters from a wide variety of plants and animals, especially for those promoters demonstrating a high level of constitutive expression and capable of maintaining stable levels of said expression under stress conditions.

The present invention is based on modifications of the plant ubiquitin regulatory system.

SUMMARY OF THE INVENTION

In one aspect the present invention provides a DNA sequence comprising a ubiquitin regulatory system lacking heatshock elements.

Because the ubiquitin regulatory system lacks heatshock elements, it is not heat inducible.

In a further aspect the invention thus provides a DNA sequence comprising a ubiquitin regulatory system that is not heat inducible substantially comprising the nucleotide sequence according to SEQ.ID.NO.8.

For brevity the ubiquitin regulatory system forming part of a DNA sequence in accordance with either of these aspects of the invention will be referred to as a modified ubiquitin regulatory system (mURS).

The mURS preferably substantially comprises a plant URS, such as a maize URS e.g. as disclosed in EP-A-0342926. The term "substantially comprises" in this context means that the mURS corresponds generally to an unmodified URS other than of course in regions where the mURS is modified, e.g. by lacking heatshock elements.

The mURS may thus comprise an intron, e.g. as disclosed in EP-A-0342926.

An mURS may be produced, e.g., by modification of an URS by removal of one or more heatshock elements therefrom, e.g. using standard DNA manipulation techniques well known to those skilled in the art.

In a further aspect the invention provides a DNA construct comprising a DNA sequence in accordance with the invention and a plant-expressible structural gene under the regulatory control of the ubiquitin regulatory system of said sequence.

The invention also provides an expression vector comprising such a DNA construct.

The mURS of the invention may be used in analogous manner as the URS described in EP-A-0342926, and reference is herewith made to that document for further details. In particular, the mURS can be used to regulate expression of an associated structural gene in cells, particularly plant cells (monocot or dicot).

The invention thus covers use of a DNA sequence, DNA construct or expression vector in accordance with the invention for transforming cells, particularly plant cells.

A further aspect of the invention provides a method of transforming a host cell, particularly a plant cell, comprising introducing into the cell a DNA sequence, DNA construct or expression vector in accordance with the invention.

Methods for achieving such transformation are well known to those skilled in the art and basically comprises the steps of constructing a plant expression vector that comprises a protein-encoding sequence and the modified ubiquitin regulatory system according to the invention and introducing the expression vector into a plant cell.

Preferably the plant cell is propagated into a plant and the protein-encoding sequence is expressed. The present invention is also a transgenic plant cell, plant and seed comprising a gene construct comprising the modified ubiquitin regulatory system.

Said plant is preferably a monocot such as wheat, barley, oat, corn or maize. Most preferably it is wheat.

The invention thus also includes within its scope a host cell, particularly a plant cell, into which has been introduced a DNA sequence, DNA construct or expression vector in accordance with the invention.

The invention further provides a method of expressing a structural gene in a host cell in a constitutive manner, the method comprising the steps of causing to be present in the host cell the structural gene, operably linked to a DNA sequence in accordance with the invention defined above and causing the structural gene to be expressed constitutively.

The modified ubiquitin regulatory system or the promoter may be truncated to determine the smallest fragment capable of expression. Methods of truncating include deleting sequences and digesting the sequence with a restriction enzyme or other nuclease with the purpose of remaining substantially the same property and/or activity as the untruncated sequence. These methods are commonly known in the art of molecular biology.

To assess promoter activity usually a transient reporter gene expression system is used. In such a system or assay, the fragment to be assayed would be linked to a reporter gene and used to transform a plant cell. Useful reporter genes include chloramphenicol acetyltransferase (CAT), luciferase (Lux) and β-glucuronidase (GUS).

The mURS of the invention functions in generally the same way as an unmodified URS except that it is not inducible in response to heat (and possibly also in response to other conditions of stress). The invention thus provides a novel regulatory system which can confer non-heat-inducible constitutive expression of associated DNA sequences. The advantage of this system is that the expression of associated DNA sequences that it mediates in transformed plant cells is stable and not influenced by environmental changes in temperature which would normally affect expression mediated by a non-modified system e.g. as described in EP-A-0342926.

The mURS has been shown to function to give high levels of constitutive expression, comparable to those obtainable from non-modified (wild-type) URS, and to be capable of maintaining stable levels of constitutive expression under conditions of heat stress.

EP-A-0342926 includes definitions of various terms that are used in the present specification, including "expression", "promoter", "regulatory control", "structural gene", "plant ubiquitin regulatory system", "heatshock elements", and "introns" and those definitions also apply to these terms when used in the present specification.

The invention will be further described, by way of illustration, in the following Examples and with reference to the accompanying drawings and Tables as well, in which:

FIG. 3 shows the predicted sequence of the mURS sequence in pPBl97-U3, with the Kpnl site which replaces the overlapping heatshock elements in the wild-type URS being boxed (this Figure corresponds to SEQ.ID.NO.8);

Tables 1 and 2 show the level of Nptll expression in each plant (expressed relative to the rRNA control) with and without heat shock treatment and the transformation event from which the plants were derived.

EXAMPLES

Example 1

Investigation of Effect on Expression of Removing the Heatshock Elements from the Ubiquitin Regulatory System Two overlapping consensus heatshock (HS) elements in the maize ubiquitin regulatory system (URS) are defined in EP 0342926 and U.S. Pat. No. 5,614,399. A modified URS (mURS) was produced as described below.

The plasmid pPBl95-1 is a derivative of pAHC25 (Christensen, A H & Quail, P H 1996. Transgenic Research 5:213–218) in which a Sacl linker sequence [d(pCGAGCTCG)] (New England Biolabs [NEB] catalogue no. 1044) has been inserted at the Smal site of pAHC25.

A mURS lacking the heatshock elements was constructed from two PCR fragments which were amplified using pPBl95-1 as template using the following primer combinations.

GUS 1: 5TCGCGATCCAGACTGAATGCC 3' (SEQ ID No: 1) with
HS1: 5'ATTAGGTACCGGACTTGCTCCGCTGTCGGC (SEQ ID No: 2). and
HS2:5'TATAGGTACCGAGGCAGCGACAGAGATGCC 3' (SEQ ID No: 3) with
Ubi5': 5'ATATGCTGCAGTGCCAGCGTGACCCGG 3' (SEQ ID No: 4).

GUS1+HS1 amplify a fragment of approximately 1330 bp. The resulting fragment has a Kpnl site (from primer HS 1) and a Sacl site (from pPBl95-1) close to its 5' and 3' ends respectively. Ubi5'+HS2 amplify a fragment of approximately 680 bp. The resulting fragment has a Pstl site (from pPBl95-1) and a Kpnl site (from primer HS 2) close to its 5' and 3' ends respectively.

Figure 1:
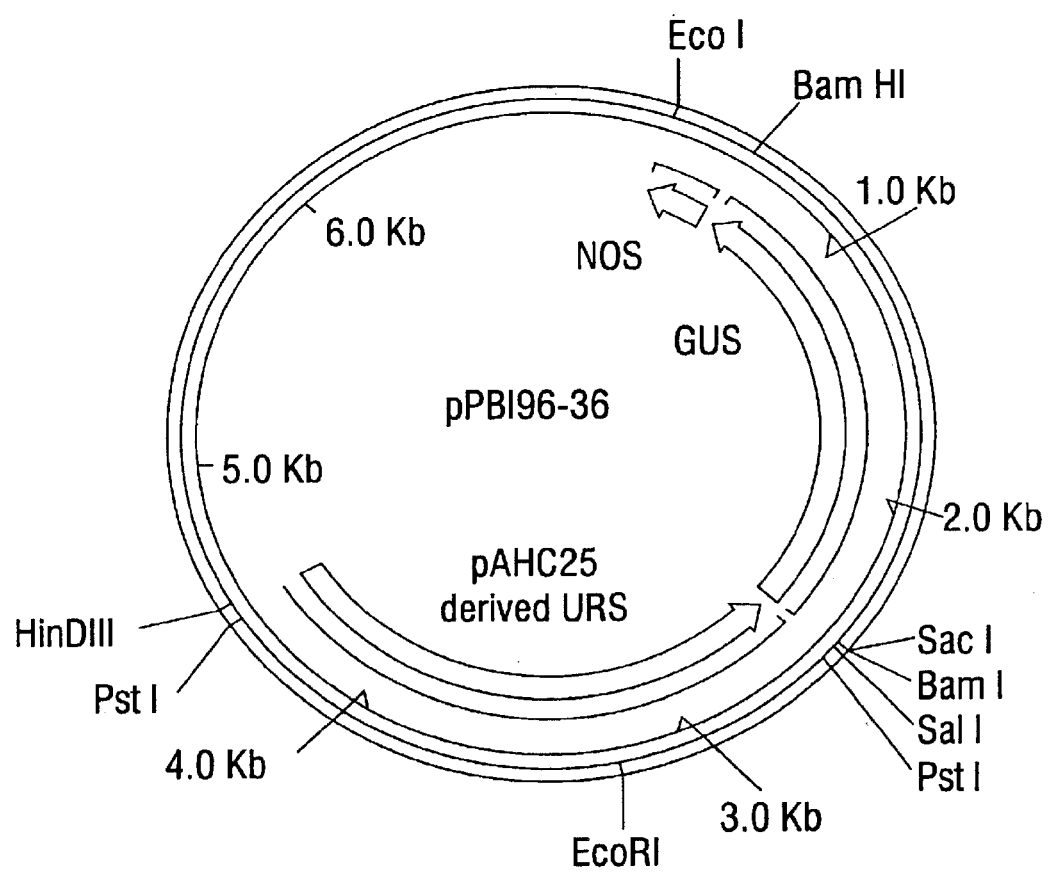
FIG. 1 is a restriction map of plasmid pPBl96-36.
Figure 2:
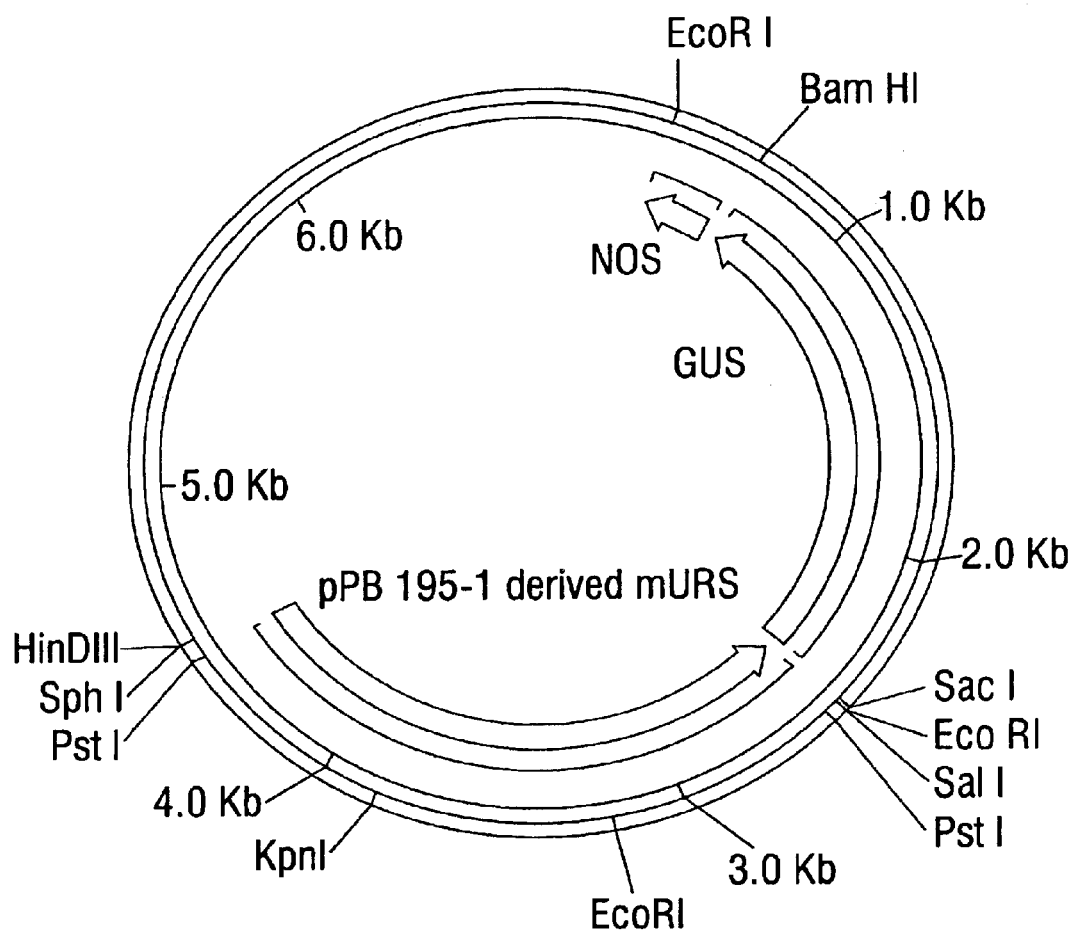
FIG. 2 is a restriction map of plasmid pdHUbiGUS.

The resulting GUS1/HS1 and Ubi5'/HS2 amplified fragments were digested with Kpnl and Sacl and with Kpnl and Pstl respectively and double ligated into the Pstl and Sacl sites of pUC19. The resulting re-constituted mURS was then transferred as a Hindlll/Sacl fragment, replacing the non-modified URS in a plasmid pPBl96-36 (FIG. 1) to produce the plasmid pdHUbiGUS (FIG. 2). The plasmid pPBl96-36 comprises the GUS-Nos reporter gene fusion under the control of the wild-type ubiquitin promoter (derived from pAHC25) in a pUC plasmid backbone.

The primer design is such that a 32 bp sequence (TGGACCCCTCTCGAGAGTTCCGCTCCACCGTT)

(SEQ ID No: 5) containing the two overlapping consensus heatshock elements in the URS defined in U.S. Pat. No. 5,614,399 are replaced by a Kpnl (GGTACC) site in the mURS.

The ability of the mURS to mediate high levels of expression of an associated DNA sequence was tested in transient GUS expression analyses by particle bombardment of pdHUbiGUS and pPBl96-36 into wheat and barley immature embryos. pPBl96-36 is identical to pdHUbiGUS except that it comprises the wild-type URS rather than the mURS. Both constructs gave rise to high levels of GUS expression as visualised by observing the number and intensity of blue foci visualised following histochemical analysis using X-gluc (methods as described in Jefferson R A [1987] Assaying chimaeric genes in plants: The GUS gene fusion system. Plant Molecular Biology Reporter 5 (4) 387–405). In fact the GUS expression mediated by the two constructs was essentially indistinguishable.

Example 2

Amplification of a mURS using Maize Genomic DNA as Template

A second mURS was prepared via PCR amplification of two DNA fragments using maize genomic DNA (maize genotype B73) as template, followed by ligation of the two fragments to produce a single fragment lacking the consensus heatshock (HS) elements. Again a Kpnl restriction site was engineered in place of the HS elements.

The PCR primers used were designed from sequence information published by Liu et al 1995 (Biochem Cell Biol 73: 19–30; database accession ZMU29159). To delete the HS element from the wild-type URS and to replace it with a diagnostic Kpnl site two fragments were amplified using the primer combinations HS1+Ubi3-3 and HS2+Ubi5-2, the sequences of which are given below. Primers Ubi5-2 and Ubi3-3 are homologous to sequences in the promoter sequence published by Liu et al. Primers HS1 and HS2 are homologous to sequences located immediately 3' and 5' respectively of the two overlapping HS elements in the ubiquitin promoter as discussed above. Both of these primers have a Kpnl tail (shown in bold in the sequences) at their 5' ends.

HS1: 5-ATTAGGTACCGGACTTGCTCCGCTGTCGGC-3 (SEQ ID No: 2)

HS2: 5-TATAGGTACCGAGGCAGCGACAGAGATGCC-3 (SEQ ID No: 3)

Ubi5: 5-AGCTGAATCCGGCGGCATGGC-3 (SEQ ID No: 6)

Ubi3-3: 5-TGATAGTCTTGCCAGTCAGGG-3 (SEQ ID No: 7)

The amplified products were subcloned into pGEM TEasy (Promega) to produce the plasmids pPBl197-1 and pPBl97-U2. Appropriate orientations for subsequent subcloning were determined by restriction digest analysis. A full-length (2 Kb) mURS sequence including the promoter and intron was reconstructed by subcloning a Kpnl—Sacl fragment from pPBl97-U1 into the Kpnl/Sacl sites of pPBl97-U2 to produce pPBl97-U3. The predicted sequence of the cloned mURS fragment in pPBl97-U3 is presented in FIG. 3 as SEQ ID No: 8. The Kpnl site which replaces the overlapping heatshock elements in the wild-type URS is boxed. pPBl97-U3 contains approximately 35 bp of sequence at its 5' end and approximately 40 bp of sequence at its 3' end, none of which is present in the plasmid pAHC25 or its derivatives.

Figure 4:
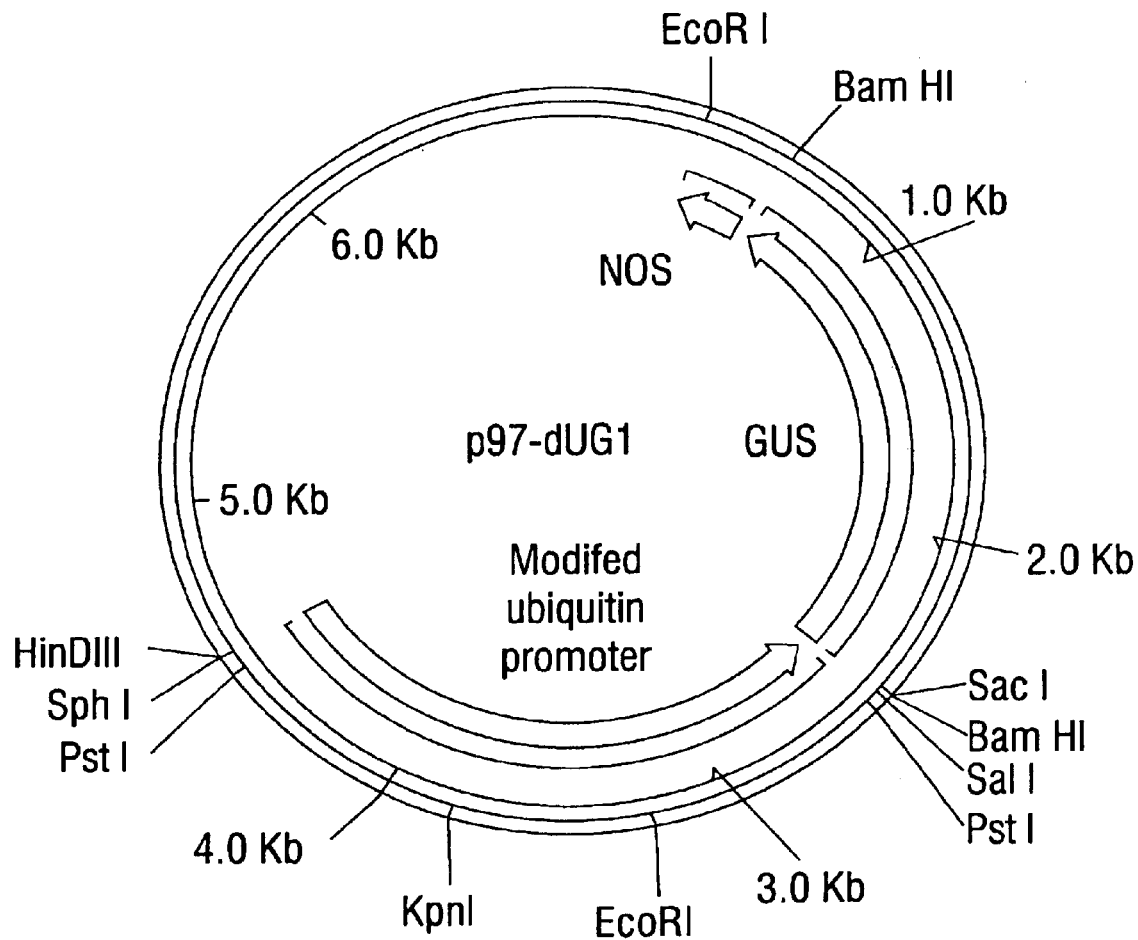
FIG. 4 is a restriction map of plasmid pPBl97-dUG1.

The mURS was transferred as a Pstl fragment from pPBl97-U3 into the Pstl sites of pPBl96-36 replacing the wild-type URS in pPBl96-36 to produce pPBl97-dUG1 (sometimes also referred to as p97-dUG1) (FIG. 4). The orientation of the modified promoter was determined using the Kpnl site which is present in the modified but not wild-type promoter. pPBl96-36 and pPBl97-dUG1 are identical except that pPBl96-36 contains the wild-type URS from pAHC25 whereas pPBl97-dUG1 contains the mURS from plasmid pPBl97-U3.

The function of the mURS in pPBl97-dUG1 was confirmed by transient transformation analyses by particle bombardment into various plant tissues and comparison with the expression mediated by the wild-type URS in pPBl96-36.

The following plant tissues were analysed: wheat and barley immature embryos, wheat leaves, wheat roots, tobacco leaves, oil palm cell suspensions.

Following bombardment the tissues were incubated at 20° C. for 24 hours prior to histochemical analysis.

The results as visualised by GUS expression were indistinguishable between the two different plasmids, indicating that deleting the heatshock sequence does not affect the capacity of the modified promoter to mediate high levels of constitutive expression in these tissues under these conditions.

Example 3

Figure 5:
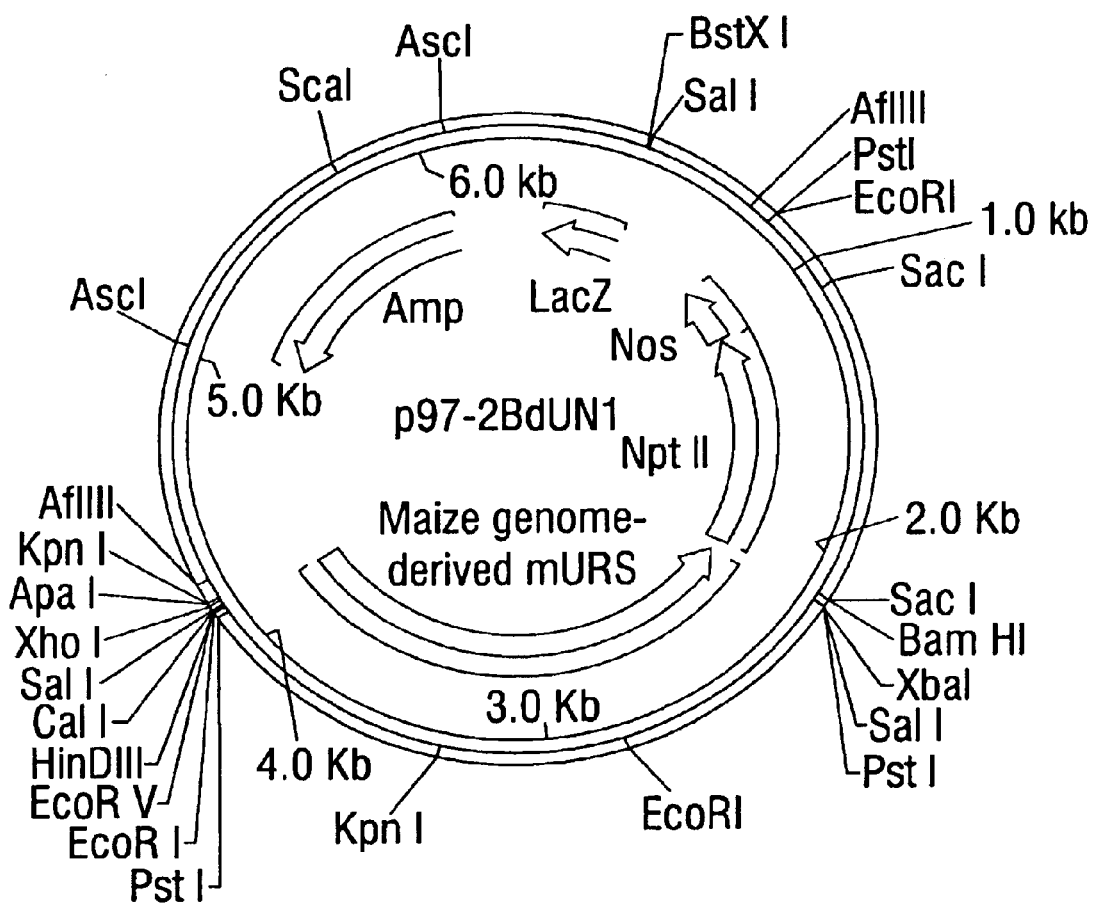
FIG. 5 is a restriction map of plasmid pPBl97-2BdUN1.

The maize genome-derived mURS in pPBl97-dUG1 has also been transferred upstream of a neomycin phosphotransferase (Nptll) sequence to produce a plasmid pPBl97-2BdUN1 (sometimes also referred to as P97-2BdUN1) (FIG. 5). This plasmid has been used successfully as a selectable marker construct in the stable transformation of wheat, as described in European Patent Application No. 98307337.0, and repeated hereafter.

Example 4

The mURS confers non-heat-inducible constitutive expression.

Plant Transformation

Figure 6:
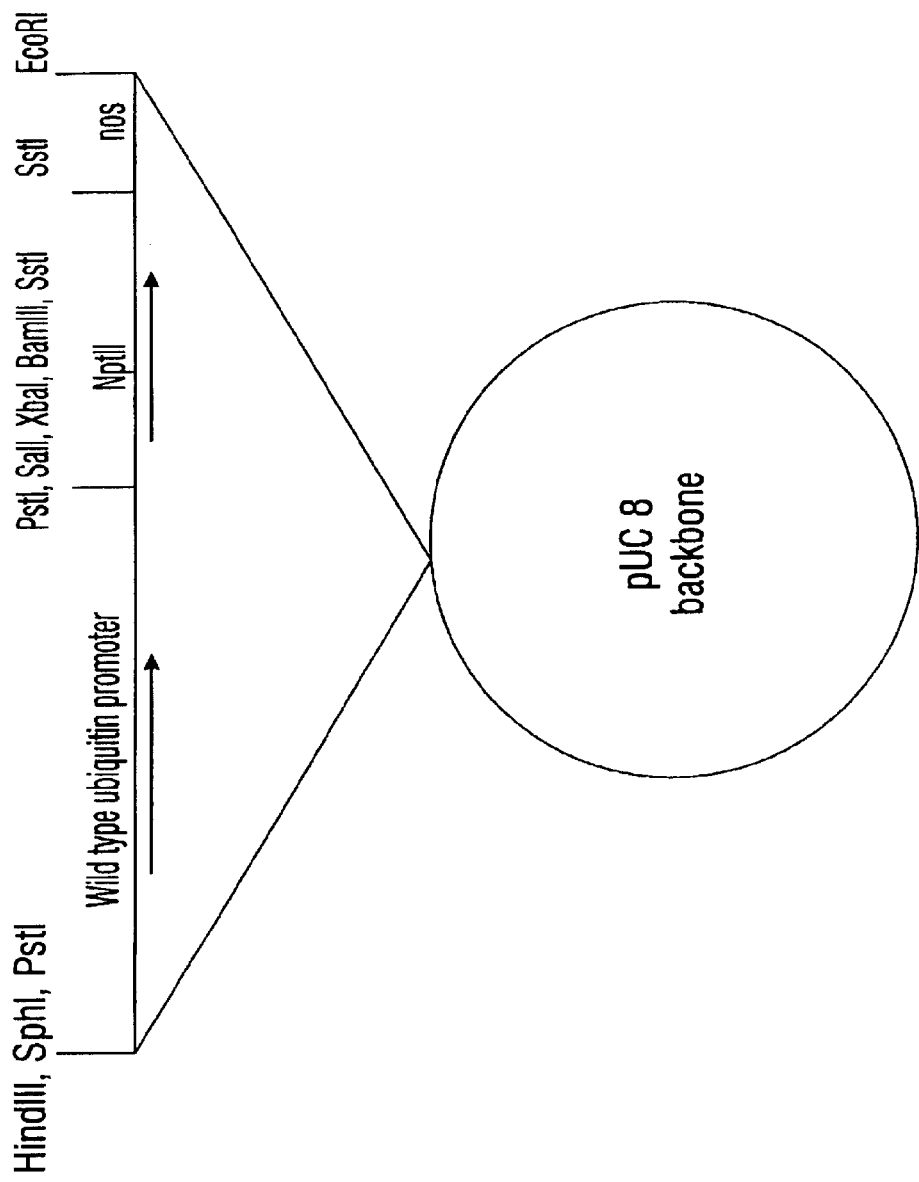
FIG. 6 shows the restriction map of plasmid pUN1 which contains the wild type URS driving the Nptll selectable marker gene.

Immature embryos (IMEs) of the wheat variety Bob White were bombarded with pPBl97 2BdUN1 which comprised the mURS driving the Nptll selectable marker gene. In independent experiments, IMEs were also bombarded with plasmid pUN1 (FIG. 6) which comprised the wild type URS driving Nptll.

A number of independent primary transformants (Ro generation) were produced.

Heat shock treatment.

A total of five events transformed with pPBl97 2BdUN1 and two events transformed with pUN1 were selected for analysis of heat inducibility. Primary transformants were allowed to set seed and the R1 seed was collected. Between 22 and 25 R1 seeds per independent event were planted and seedlings were tested for Nptll activity via leaf bleach assay. A total of 8–12 Nptll leaf bleach assay positive plants from each original event were selected and grown in a glasshouse to the 2–3 leaf stage. Plants were then removed from the glasshouse and 4–6 plants from each event were heat shocked for 2 hours at 42 degrees C. in a Vulcan™ incubator, while 4–6 plants from each event were left at room temperature, i.e. non heat shocked. Leaf material was harvested from all lines, both heat shocked and non heat shocked, and stored at −70° C. prior to analysis.

RNA Isolation and Northern Blotting

Frozen leaf tissue from each plant was ground to a fine powder under liquid nitrogen in a Braun Mikrodismembrator™. Total RNA was extracted from approximately 100 mg frozen ground tissue using the Qiagen Rneasy™ extraction kit according to manufacturers instructions. 15 μg of total RNA was electrophoresed on a 1% agarose, 2.21M formaldehyde, 40 mM MOPS pH7.0, 10 mM sodium acetate, 1 mM EDTA gel, in a 40 mM MOPS pH 7, 10 mM sodium acetate, 1 mM EDTA running buffer at 1 V/cm overnight. Gels were washed briefly in sterile distilled $H_2O$, and blotted onto HyBond $N^+$ (Amersham International), according to standard protocols (Sambrook et al, 1989) overnight Blots were then dismantled and airdried for 2 hours, before UV fixing at 312 nm for 2 minutes.

Probe Labelling and Hybridization 25 ng of the appropriate probe (Nptll, or wheat ribosomal 25S fragment) were radiolabelled using the Rediprime 11 ™system (Amersham International) using α $^{32}$PdCTP (Amersham International) according to manufacturers instructions. Blots were hybridized overnight at 65° C. in 0.6M NaCl, 20 mM Pipes, 4 mM $Na_2EDTA.2H_2O$, 0.2% gelatin, 0.2% Ficoll1400, 0.2% PVP-360, 10 mM $Na_4P_2O_7.10H_2O$, 0.8% SDS, 0.5 mg/ml denatured salmon sperm DNA. Post hybridization washes were carried out in 30 mM NaCl, 2Mm $NaH_2PO_4.2H_2O$, 0.2 mM $Na_2EDTA.2H_2O$, 0.1% SDS at room temperature for 30 minutes, then 65° for 10 minutes. Blots were exposed to Typhoon™ General Purpose phosphorimager screens for 1–2 days depending on signal strength, and the screens were scanned on the Typhoon™ Phosphorimager to quantitate signal intensity.

The Nptll expression was determined relative to the ribosomal-RNA level in order to standardise variation in total RNA loading.

Results

Figure 7A:
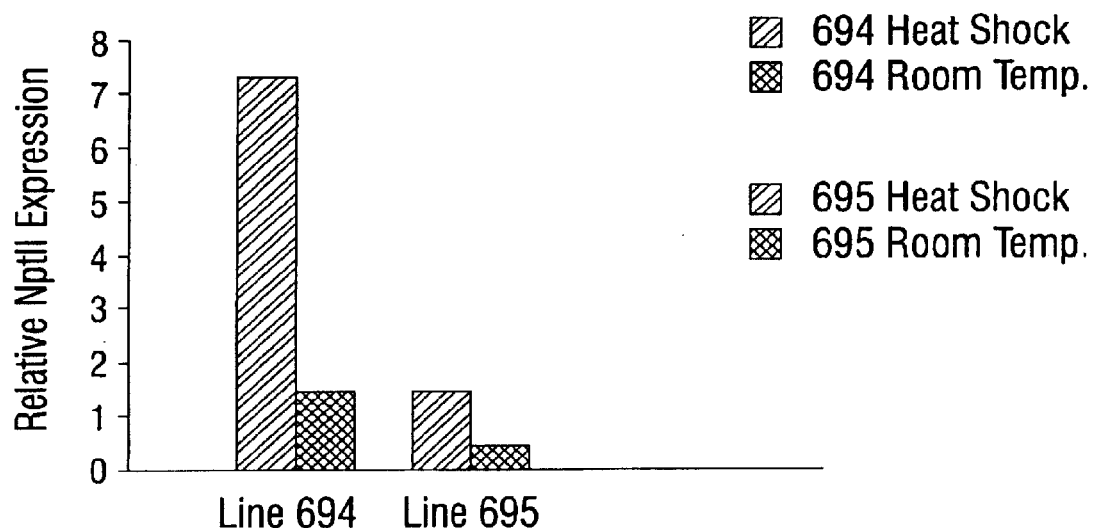
FIG. 7 is a bar chart showing the mean relative level of Nptll expression from each transformation event after heat shock (grey) and without heat shock (black). Results from lines transgenic for the wild type URS are shown in panel (a) and results from the mURS are shown in panel (b).

The relative expression of Nptll in progeny from two independent events (lines 694 and 695) transformed with pUN1 (wild type URS) is shown (Table 1). The mean level of expression in progeny from line 694 after heat shock was 5× higher than in progeny maintained at room temperature (FIG. 7a). Similarly, expression in progeny from line 695 showed a 3.4× induction after heat shock (FIG. 7a). This confirms that the wild type URS is heat inducible.

Figure 7B:
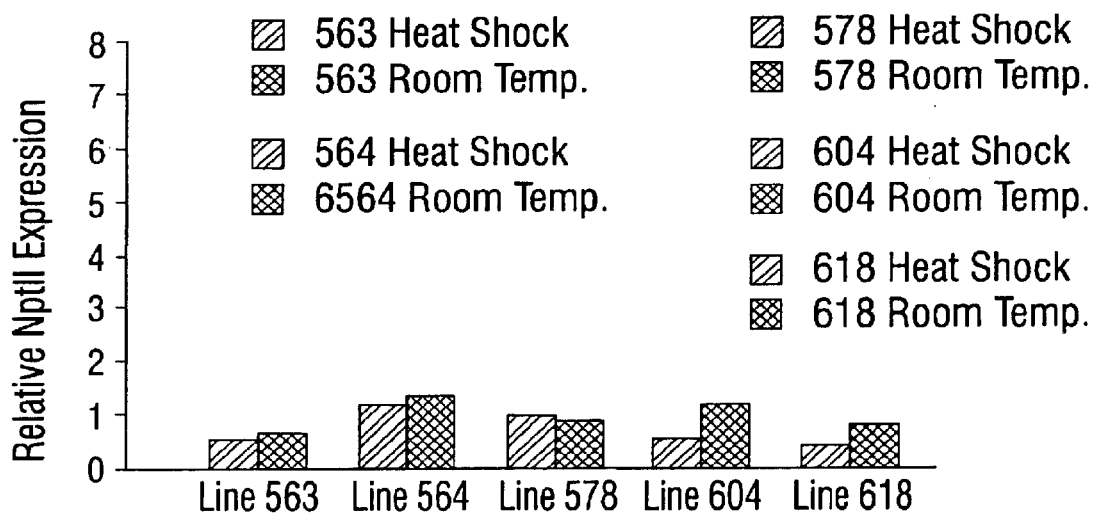

The relative expression of Nptll in progeny from five independent events (lines 563, 564, 578, 604, 618) transformed with pPBl97 2BdUN1 (mURS) is shown (Table 2). In all lines, the mean level of expression after heat shock was either less than or approximately equal to that in plants maintained at room temperature indicating that expression from the mURS is not heat inducible (FIG. 7b). This demonstrates that removal of the heat shock elements from the URS leads to a non-heat inducible pattern of expression.

TABLE 1

| Wild Type URS | Plant number | Heat Shock Relative Nptll expression | Mean | Plant number | Room Temp Relative Nptll expression | Mean |
|---|---|---|---|---|---|---|
| Line 694 | 1 | 3.38 | 7.30 | 14 | 1.22 | 1.44 |
| | 2 | 6.78 | | 10 | 1.27 | |
| | 3 | 9.67 | | 11 | 2.23 | |
| | 5 | 6.39 | | 12 | 1.03 | |
| | 6 | 10.3 | | | | |
| Line 695 | 1 | 1.32 | 1.43 | 2 | 0.47 | 0.42 |
| | 4 | 1.4 | | 5 | 0.38 | |
| | 12 | 0.83 | | 9 | 0.32 | |
| | 13 | 0.72 | | 10 | 0.47 | |
| | 7 | 2.88 | | 23 | 0.47 | |

TABLE 2

| Modified URS | Plant number | Heat Shock Relative Nptll expression | Mean | Plant number | Room Temp Relative Nptll expression | Mean |
|---|---|---|---|---|---|---|
| Line 563 | 1 | 0.28 | 0.48 | 12 | 0.61 | 0.61 |
| | 11 | 0.30 | | 13 | 0.51 | |
| | 6 | 0.44 | | 14 | 0.57 | |
| | 7 | 0.44 | | 15 | 0.27 | |
| | 8 | 0.92 | | 16 | 1.1 | |
| Line 564 | 1 | 0.93 | 1.17 | 3 | 1.06 | 1.32 |
| | 7 | 1.92 | | 4 | 1.34 | |
| | 9 | 1.06 | | 5 | 1.24 | |
| | 10 | 0.88 | | 19 | 1.15 | |
| | 16 | 1.04 | | 23 | 1.82 | |
| Line 578 | 12 | 1.14 | 0.94 | 3 | 0.87 | 0.84 |
| | 13 | 1.31 | | 4 | 0.66 | |
| | 14 | 0.9 | | 6 | 1.02 | |
| | 18 | 0.61 | | 7 | 0.88 | |
| | 19 | 0.72 | | 21 | 0.75 | |
| Line 604 | 1 | 0.91 | 0.47 | 8 | 0.91 | 1.14 |
| | 2 | 0.12 | | 10 | 1.64 | |
| | 3 | 0.1 | | 11 | 1.21 | |
| | 4 | 0.45 | | 18 | 0.78 | |
| | 16 | 0.77 | | | | |
| Line 618 | 2 | 0.28 | 0.32 | 10 | 1.12 | 0.71 |
| | 3 | 0.44 | | 11 | 0.65 | |
| | 15 | 0.3 | | 14 | 0.47 | |
| | 16 | 0.4 | | 6 | 0.73 | |
| | 18 | 0.24 | | 8 | 0.85 | |
| | 19 | 0.23 | | 9 | 0.42 | |

Methods and Materials Used in the Examples Described Above

The wheat transformation method used and described here is largely based on the method disclosed by Barcelo and Lazzeri (1995): Transformation of cereals by microprojectile bombardment of immature inflorescence and scutellum tissues; Methods in Molecular Biology-Plant Gene Transfer and Expression Protocols (vol 49), 113–123; Jones H (ed) Humana Press Inc., Totowa, N.J.

Embryo wheat plants of the spring cultivar Bob White were grown in a glasshouse with 16 hr day length supplemented with lights to maintain a minimum light intensity of 500 μmol $m^{-2}s^{-1}$ at 0.5M above flag leaf. Glasshouse temperatures were maintained at 19° C.+/−1° C. during the day and 14° C.+/−1° C. at night.

Immature embryos of wheat were harvested from developing grain. The seeds were harvested and embryos were cultured at approximately 12 days after anthesis when the embryos were approximately 1 mm in length. Seeds were first rinsed in 70% ethanol for 5 minutes and then sterilised in a 10% solution of Domestos bleach (Domestos is a Trade Mark) for 15 minutes followed by 6 washes with sterile distilled water. Following removal of the embryonic axis the embryos were placed axis surface face down on agargel (Sigma catalogue no. A-3301) solidified MM1 media. The general recipe for MM1 is given In Appendix 1, and the recipes for the various constituents in Appendix 2. The embryos were maintained in darkness for one to two days at 24° C.+/−1° C. prior to bombardment.

The plasmids pUN1 and p97-2BdUN1 were used to provide selection markers. The plasmids pUN1 and p97-2BdUN1 contain chimeric promoter-Nptll gene fusions and provide selection of transformants against a range of aminoglycoside antibiotics including kanamycin, neomycin, geneticin and paromycin.

Particle bombardment was used to introduce plasmids into plant cells. The following method was used to precipitate plasmid DNA onto 0.6 μm gold particles (BIO-RAD catalogue number 165–2262): A total of 5 µg of plasmid DNA was added to a 50 µl—sonicated for one minute—suspension of gold particles (10 mg/ml) in a 1.5 ml microfuge tube. Following a brief vortex for three seconds 50 µl of a 0.5M solution of calcium chloride and 20 µl of a 0.05M solution of spermidine free base were added to the opposite sides of the microfuge tube lid. The tube contents were mixed together by closing the lid and tapping the calcium chloride and spermidine to the bottom of the tube. Following a vortex for three seconds the suspension was centrifuged at 13,000 rpm for 5 seconds. The supernatant was then removed and the pellet resuspended in 150 µl of absolute ethanol. This requires scraping the gold particles off the inside of the tube using a pipette tip. Following a further three second vortex, the sample was centrifuged again and the pellet resuspended in a total volume of 85 µl in absolute ethanol. The particles were vortexed briefly and sonicated for 5 seconds in a Camlab Trisonic T310 water bath sonicator to ensure fine dispersion. An aliquot of 5 µl of the DNA coated gold particles were placed in the centre of a macrocarrier (BIO-RAD catalogue no. 115–2335) and allowed to dry for 30 mins. Particle bombardment was performed by using a Biolisite™ PDS-1000/He (BIO-RAD Instruments, Hercules Calif.) chamber which is illustrated schematically in FIG. 8, using helium pressure of 650 and 900 psi (rupture discs: BIO-RAD catalogue numbers 165–2327 and 165–2328 respectively).

Referring to FIG. 8, the illustrated vacuum chamber comprises a housing 10, the inner side walls of which include a series of recesses 12 for receiving shelves such as sample shelf 14 shown at the fourth level down from the top of the housing. A rupture disc 16 is supported in a He pressure shock tube 18 near the top of the housing. A support 20, resting in the second set of recesses 12 down from the top of the housing, carries unit 22 that includes a stopping screen and a number of rings 24, with 11 rings below the support 20 and 3–4 rings above the support 20. Macrocarrier 26 is supported at the top of unit 22. The approximate distance from the rupture disc 16 to the macrocarrier 26 is 25 mm, with the approximate distance from the macrocarrier 26 to the stopping screen being 7 mm, and the approximate distance from the stopping screen to the sample shelf 14 being 67 mm. The top of unit 22 is about 21 mm from the bottom of the shock tube 18, and the bottom unit 22 is about 31 mm from the top of sample shelf 14.

Immature embryos were bombarded between 1 and 2 days after culture. For bombardment the immature embryos were grouped into a circular area of approximately 1 cm in diameter comprising 20–100 embryos, axis side face down on the MM1 media. A petri dish containing the tissue was placed in the chamber on shelf 14, on the fourth shelf level down from the top, as illustrated in FIG. 8. The air in the chamber was then evacuated to a vacuum of 28.5 inches of Hg. The macrocarrier 26 was accelerated with a helium shock wave using rupture membranes that burst when the He pressure in the shock tube 18 reaches 650 or 900 psi. Within 1 hour after bombardment the bombarded embryos were plated on MM1 media at 10 embryos per 9 cm petri dish and then maintained in constant darkness at 24° C. for 2–3 weeks. During this period somatic embryogenic callus was produced on the bombarded embryos.

After 2–3 weeks the embryos were transferred onto agar-solidified regeneration media, known as R media, and incubated under 16 hr day length at 24° C. The general recipe for R media is given in Appendix 1. Embryos were transferred on fresh plates at 2–3 week intervals. For selection of transformants using the NptII gene three different regimes were used: 1) Geneticin (GIBCO-BRL catalogue no. 10131-019) was incorporated (at 50 mg/L) immediately on transfer to regeneration media and maintained at 50 mg/L on subsequent transfers to regeneration media. 2) & 3) Embryos were first transferred to regeneration media without selection for 12 days and 2–3 weeks, respectively, and thereafter transferred on to media containing Geneticin at 50 mg/L. After 2–3 passages on regeneration media regenerating shoots were transferred to individual culture tubes containing 15 ml of regeneration media at half salt strength with selection at 35 mg/L geneticin. Following root formation the regenerated plants were transferred to soil and the glass house.

Leaf Bleach Assay

Primary transformants and progeny were confirmed as transgenic by leaf bleach assay as described in Plant Physiol. (1997) 115: 971–980. Leaf pieces were vacuum infiltrated with paromomycin and scored for resistance after 2–3 days. This method was validated by comparison with results from analysis of genomic DNA via Southern blotting.

Genomic DNA Isolation and Southern Analyses

Southern analyses of primary transformants and progeny material were carried out as follows: Freeze dried leaf tissues were ground briefly in a Kontes™ pestle and mortar, and genomic DNA extracted as described in Fulton et al, 1995. 5 µg of DNA were digested with an appropriate restriction enzyme according to the manufacturers instructions, and electrophoresed overnight on a 1% agarose gel, after which the gel was then photographed, washed and blotted onto Hybond N+™(Amersham International) according to the method of Southern using standard procedures (Sambrook et al 1989, Molecular Cloning: A Laboratory Manual, 2$^{nd}$ ed. Cold Spring Harbour Press, Cold Spring Harbour, N.Y.). Following blotting, the filters were air dried, baked at 65° C. for 1–2 hours and UV fixed at 312 nm for 2 minutes.

Probe preparation and labelling for the Southern analyses of transformed material was carried out as described above.

GUS histochemistry was performed essentially as described in Jefferson (1987), Plant Molecular Biology Reporter,5,(4),387–405.

Appendix 1

Recipe for 2× Concentrated MM1 media

| Constituent | Volume of stock per liter of 2x concentrated media |
|---|---|
| Macrosalts MS (10X stock) | 200 ml |
| Microsalts L (1000x stock) | 2 ml |
| FeNaEDTA MS (100x stock) [Sigma catalogue F-0518] | 20 ml |
| Modified Vits MS (x1000) | 1 ml |
| 3 amino acid solution (25x stock) | 40 ml |
| myo inositol (Sigma catalogue number I-3011) | 0.2 g |
| sucrose | 180 g |
| AgNO$_3$ (20 mg/ml stock) Added after filter sterilisation | 1 ml |
| Picloram (1 m/ml stock) Added after filter sterilisation | 4 ml |

Filter sterilise and add to an equal volume of moulten 2× agar (10 g/liter)

Recipe for 2× Concentrated R Media

| Constituent | Volume of stock per liter of 2× concentrated media |
| --- | --- |
| Macrosalts L7 (10X stock) | 200 ml |
| Microsalts L (1000x stock) | 2 ml |
| FeNaEDTA MS (100x stock) | 20 ml |
| Vits/Inositol L2 (200x stock) | 10 ml |
| 3 amino acid solution (25x stock) | 40 ml |
| Maltose | 60 g |
| 2,4-D (1 mg/ml stock) added after filter sterilisation | 200 µl |
| Zeatin cis trans mixed isomers (Melford labs catalogue no. Z-0917) (5 mg/ml stock) added after filter sterilisation | 2 ml |

Filter sterilise and add to an equal volume of moulten 2× agar (16 g/litre).

Appendix 2

Recipes for constituents of MM1 and R media Microsalts L (1000× stock)

|  | per 100 ml |
| --- | --- |
| $MnSO_4.7H_2O$ | 1.34 g |
| $H_3BO_3$ | 0.5 g |
| $ZnSO_4.7H_2O$ | 0.75 g |
| KI | 75 mg |
| $Na_2MoO_4.2H_2O$ | 25 mg |
| $CuSO_4.5H_2O$ | 2.5 mg |
| $CoCl_2.6H_2O$ | 2.5 mg |

Filter sterilise through a 22 µm membrane filter Store at 4° C.

Macrosalts MS (10× stock)

|  | per liter |
| --- | --- |
| $NH_4NO_3$ | 16.5 g |
| $KNO_3$ | 19.0 g |
| $KH_2PO_4$ | 1.7 g |
| $MgSO_4.7H_2O$ | 3.7 g |
| $CaCl_2.2H_2O$ | 4.4 g |

NB: Dissolve $CaCl_2$ before mixing with other components
NB: Make up $KH_2PO_4$ separately in sterile $H_2O$, and add last Store solution at 4° C. after autodaving Modified MS Vits (1000× stock)

|  | Per 100 ml |
| --- | --- |
| Thiamine HCl | 10 mg |
| Pyridoxine HCl | 50 mg |
| Nicotinic acid | 50 mg |

Store solution in 10 ml aliquots at −20° C.

3 amino acid solution (25× stock)

|  | Per liter |
| --- | --- |
| L-Glutamine | 18.75 g |
| L-Proline | 3.75 g |
| L-Asparagine | 2.5 g |

Store solution in 40 ml aliquots at −20° C.

Macrosalts L7 (10× stock)

|  | per liter |
| --- | --- |
| $NH_4NO_3$ | 2.5 g |
| $KNO_3$ | 15.0 g |
| $KH_2PO_4$ | 2.0 g |
| $MgSO_4.7H_2O$ | 3.5 g |
| $CaCl_2.2H_2O$ | 4.5 g |

NB: Dissolve $CaCl_2$ before mixing with other components
NB: Make up $KH_2PO_4$ separately in 50 ml $H_2O$ and add last
Store solution at 4° C. after autoclaving Vits/Inositol (200× stock)

| Vits/Inositol (200x stock) | |
| --- | --- |
| 200x Stock | Per 100 ml |
| Inositol | 4.0 g |
| Thiamine HCl | 0.2 g |
| Pyridoxine HCl | 0.02 g |
| Nicotinic acid | 0.02 g |
| Ca-pantothenate | 0.02 g |
| Ascorbic acid | 0.02 g |

Store solution in 40 ml aliquots at −20° C.

What is claimed is:

1. An isolated DNA sequence comprising a ubiquitin regulatory system lacking heat shock elements wherein the ubiquitin regulatory system comprises the nucleotide sequence according to SEQ.ID.NO. 8.

2. A DNA construct comprising the DNA sequence of claim 1 operably linked to a plant-expressible structural coding sequence.

3. An expression vector comprising a DNA construct in accordance with claim 2.

4. A method of transforming a host cell by introducing into the cell the DNA sequence of claim 1, the DNA construct of claim 2 or the expression vector of claim 3.

5. A method according to claim 4 wherein the host cell is a plant cell.

6. A host cell transformed with the DNA sequence of claim 1, the DNA construct of claim 2, or the expression vector of claim 3.

7. A method of expressing a structural sequence in a host cell in a constitutive manner comprising transforming the host cell with the DNA sequence of claim 1, the DNA construct of claim 3, or the expression vector of claim 3, wherein the structural coding sequence is constitutively expressed in the host cell.

8. A transgenic plant comprising the DNA sequence of claim 1, the DNA construct of claim 2, or the expression vector of claim 3.

9. The transgenic plant of claim 8 wherein the plant is a monocot selected from the group consisting of wheat, barley, oat, corn or maize.

10. A transgenic plant seed comprising the DNA sequence of claim 1, the DNA construct of claim 2, or the expression vector of claim 3.

* * * * *

UNITED STATES PATENT AND TRADEMARK OFFICE
CERTIFICATE OF CORRECTION

PATENT NO. : 6,878,818 B1
DATED : April 12, 2005
INVENTOR(S) : Andrew Goldsbrough It is certified that error appears in the above-identified patent and that said Letters Patent is hereby corrected as shown below:

Column 17,
Line 9, after "structural" insert -- coding --.
Line 12, delete first instance of "claim 3" and insert -- claim 2 -- therefor.

Signed and Sealed this

Fifth Day of July, 2005

JON W. DUDAS
*Director of the United States Patent and Trademark Office*